(12) United States Patent
Suzuki et al.

(10) Patent No.: US 9,375,364 B2
(45) Date of Patent: Jun. 28, 2016

(54) ABSORBENT ARTICLE

(75) Inventors: Migaku Suzuki, Tokyo (JP); Yoshio Hirai, Tokyo (JP)

(73) Assignee: DAIO PAPER CORPORATION, Shikokuchuo (JP)

(*) Notice: Subject to any disclaimer, the term of this patent is extended or adjusted under 35 U.S.C. 154(b) by 0 days.

(21) Appl. No.: 14/385,062

(22) PCT Filed: Mar. 15, 2012

(86) PCT No.: PCT/JP2012/056715
§ 371 (c)(1),
(2), (4) Date: Sep. 12, 2014

(87) PCT Pub. No.: WO2013/136486
PCT Pub. Date: Sep. 19, 2013

(65) Prior Publication Data
US 2015/0032071 A1    Jan. 29, 2015

(51) Int. Cl.
*A61F 13/15*    (2006.01)
*A61F 13/495*    (2006.01)
*A61F 13/49*    (2006.01)
*A61F 13/494*    (2006.01)

(52) U.S. Cl.
CPC ......... *A61F 13/495* (2013.01); *A61F 13/49017* (2013.01); *A61F 13/49406* (2013.01); *A61F 2013/4951* (2013.01); *A61F 2013/4953* (2013.01); *A61F 2013/4956* (2013.01); *A61F 2013/49092* (2013.01)

(58) Field of Classification Search
CPC .............. A61F 13/495; A61F 13/4951; A61F 13/4953; A61F 13/4956; A61F 13/49473
See application file for complete search history.

(56) References Cited

U.S. PATENT DOCUMENTS

| | | | |
|---|---|---|---|
| 7,842,019 B2 | 11/2010 | Sugiyama et al. | |
| 8,157,778 B2 | 4/2012 | Moriya et al. | |
| 2006/0241557 A1* | 10/2006 | Moriya | A61F 13/494 604/385.08 |

(Continued)

FOREIGN PATENT DOCUMENTS

| | | |
|---|---|---|
| JP | A-2002-011044 | 1/2002 |
| JP | A-2002-143217 | 5/2002 |
| JP | A-2002-204811 | 7/2002 |

(Continued)

OTHER PUBLICATIONS http://www.merriam-webster.com/dictionary/bag, 20151027.*

(Continued)

*Primary Examiner* — Bradley Philips
(74) *Attorney, Agent, or Firm* — Oliff PLC

(57) ABSTRACT

An absorbent article includes: an absorbent article body part having a first leak preventer and an absorber; a second leak preventer arranged above the absorber having an enclosed space formed in bag form on a lower side by sealing a periphery part save a front end part to the absorbent article body part; a skin contact sheet arranged between front and rear parts of the absorbent article body part, contacts a wearer's skin and is spaced apart from the absorber at parts other than front and rear end parts; and a urine/feces separation member, wherein a front or middle part couples to a corresponding crotch part of the skin contact sheet, a rear part extends, on a lower side of the second leak preventer, up to at least the front end part of the second leak preventer, and right and left side parts couple to the absorbent article body part.

7 Claims, 5 Drawing Sheets

(56) References Cited

U.S. PATENT DOCUMENTS

Figure 1:
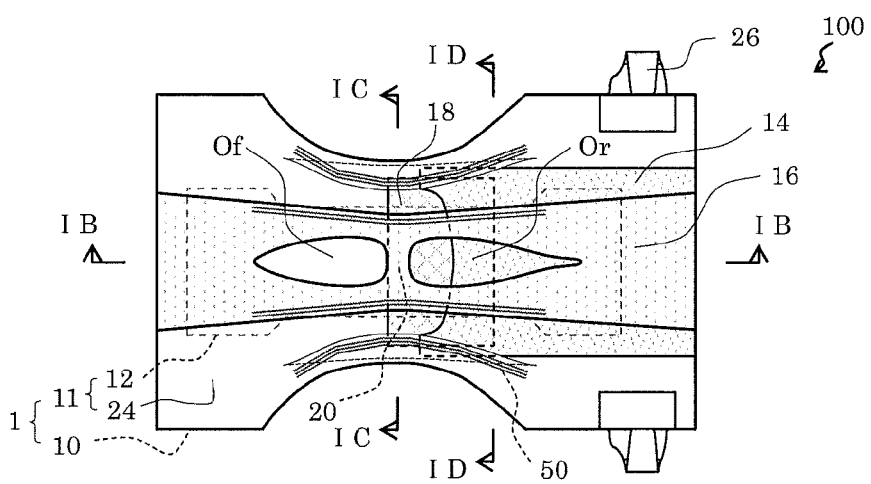
Figure 1:
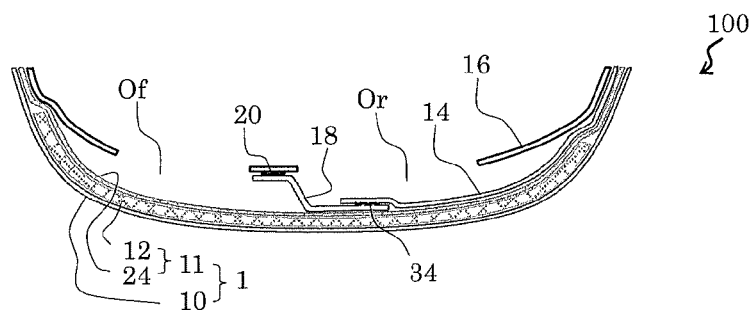
Figure 1:
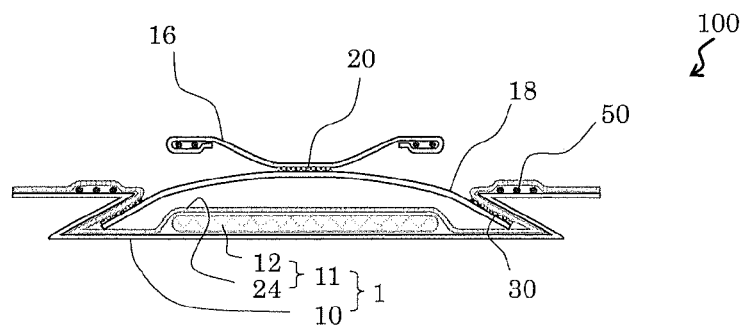
Figure 1:
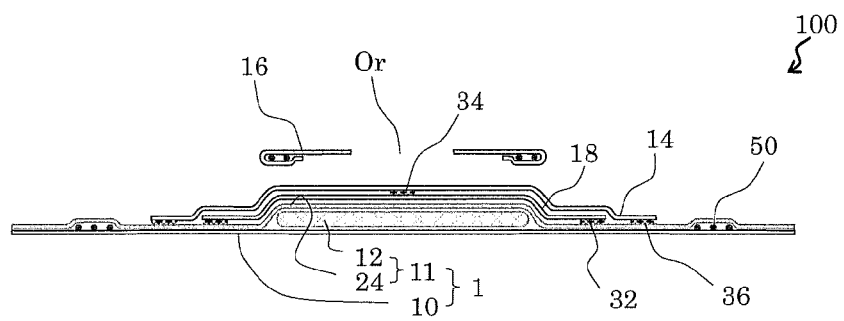

2007/0088310 A1    4/2007    Katsuhiko et al.
2009/0005752 A1    1/2009    Suzuki et al.

FOREIGN PATENT DOCUMENTS

| JP | A-2006-055308 | 3/2006 |
| JP | 2006-116157 A | 5/2006 |
| JP | A-2007-190315 | 8/2007 |
| JP | A-2007-236911 | 9/2007 |
| JP | A-2008-086428 | 4/2008 |
| JP | A-2009-089845 | 4/2009 |
| JP | A-2009-219744 | 10/2009 |

OTHER PUBLICATIONS www.google.com/definition_of_enclosed; 02012016.*
http://www.thefreedictionary.com/seal; 02012016.*
Jun. 19, 2012 International Search Report issued in International Application No. PCT/JP2012/056715.
Jun. 19, 2012 Written Opinion issued in International Application No. PCT/JP2012/056715 (with translation).
May 15, 2012 Office Action issued in Japanese Application No. 2012-514256 (with translation).
Oct. 26, 2015 Search Report issued in European Patent Application No. 12870966.4.

* cited by examiner

A

B

ABSORBENT ARTICLE

FIELD OF THE INVENTION

The present invention relates to an absorbent article.

BACKGROUND ART

Absorbent articles such as paper diapers (for infants and adults), sanitary napkins, incontinence articles, training pants or the like are articles that absorb bodily fluids such as urine excreted from a wearer by means of an absorber that makes use of wooden pulp, a super absorbent polymer (hereinafter referred to as "SAP") or the like.

Conventionally, the outermost surface has been the top sheet and it had a configuration in which a wearer's skin was in constant contact with excreted urine and feces and also had a configuration in which urine and feces were mixed, since both urine and feces were received thereon.

In this way, when the excreted urine and feces made contact with the wearer's skin, problems such as staining, a feeling of discomfort, rashes and the like would occur. Additionally, when the urine and feces were mixed, the pH value of the urine changes, and thus, problems, such as rashes being prone to arise and odors becoming stronger, would occur.

On the other hand, it is known to provide a skin contact sheet which is made to abut the wearer in a closely-attached condition by a resilient member and which has an opening for the permeation of feces (see Patent Documents 1 to 3). The absorbent articles described in Patent Documents 1 to 3 have a configuration in which a skin contact sheet is arranged above the outermost surface such that it floats from the top surface of the absorber and is constantly in a closely-attached condition with the skin, such that contact with excreted urine and feces is avoided, and a urine/feces contact sheet, an absorber, and a urine/feces barrier sheet above the rear surface are arranged in this order from the top.

In addition, it is known that, by means of a configuration in which a bridging member or the like, which is provided so as to laterally traverse an internal space in the absorbent article so as to separate such internal space into a front space and a back space, is provided so as to stand up from the absorber, urine is received in the front side space and feces are received in the rear side space and thus, contact with the urine and feces is prevented (see Patent Document 4).

Moreover, as an absorbent article which can effectively separate urine and feces and which has a high urine absorption capacity, an absorbent article provided with: a first leak preventer in sheet form; a second leak preventer in sheet form, which is present at a rear part of a top part of the first leak preventer; and an absorber which contains a super absorbent polymer and which is capable of absorbing a bodily fluid, wherein at least one layer thereof is arranged from a front part of the top part of the first leak preventer to a lower side of the second leak preventer, is known (see Patent Document 5).

PRIOR ART REFERENCES

Patent Documents

Patent Document 1: Japanese Laid-Open Patent Application No. 2002-011044
Patent Document 2: Japanese Laid-Open Patent Application No. 2002-143217
Patent Document 3: Japanese Laid-Open Patent Application No. 2002-204811
Patent Document 4: Japanese Laid-Open Patent Application No. 2007-236911
Patent Document 5: Japanese Laid-Open Patent Application No. 2006-055308

SUMMARY OF THE INVENTION

Problems to be Solved by the Invention

However, according to the inventors' review, the absorbent articles described in Patent Documents 1 to 3 have the following problem regarding the configuration of the outermost surface which makes contact with a wearer's skin. Namely, as described above, since the newly-introduced skin contact sheet is only fixed at the front and rear end parts, and thus, there are no other fixing points, it has a fatal flaw to the effect that, when it is used, a positional displacement occurs in the lateral and front-and-back directions, in particular, at the important central crotch part and, thus, the position thereof is not stable.

Additionally, according to the inventors' review, the absorbent article described in Patent Document 4 has the following problem regarding the configuration of a bridging member that performs a urine/feces separation function. Namely, in the absorbent article described in Patent Document 4, in order for a bridging member to perform a urine/feces separation function, it is substantially necessary to make use of a stretchable material as the bridging member. This is because the shape of the bridging member in the vicinity of the perineum of the wearer needs to be deformable in accordance with relatively large shape of the irregularities of the perineum, and because various movements, including vertical, front-rear and lateral movements, derived from the wearer's body positions and actions need to be followed. However, when such stretchable material is used, there are problems to the effect that the material costs increase and production apparatuses become complex and thus, production costs also increase.

Moreover, according to the inventors' review, the absorbent article described in Patent Document 5 has a problem to the effect that urine absorbed in the absorber in the rear body transfers onto the second leak preventer. Namely, in the absorbent article described in Patent Document 5, urine is received by an absorber which is present at a top part of a first leak preventer and feces are received by a second leak preventer, and preferably, it is intended that the contact between urine and feces is prevented, as long as the urine does not overflow onto the second leak preventer and/or the feces do not overflow onto the absorber, by providing a urine/feces stopping member at a front end part, or in the vicinity thereof, of the second leak preventer. However, in reality, when, for example, the amount of the excreted urine reaches close to a limit of the absorption capacity of the absorber due to prolonged usage or the like, the urine, which is not absorbed and thus stays at the rear body part of the absorber, seeps out from a gap present at the periphery part of the second leak preventer toward a top part, i.e. onto the second leak preventer. Thus, there is a problem to the effect that the urine makes contact and mixes with feces already excreted onto the second leak preventer or with feces that may be excreted later.

An object of the present invention is to provide an absorbent article, which has a basic function of a skin contact sheet that is present so as to float from the surface of an absorber, which has no positional displacement at the crotch part, which can effectively avoid contact between a wearer's skin and urine/feces, and which can be produced at a low cost.

Means for Solving the Problems

As result of diligently conducting research so as achieve the object set forth above, the present inventors have found that an absorbent article, which has a basic function of a skin contact sheet that is present so as to float from the surface of an absorber, which has no positional displacement at the crotch part, which can effectively avoid contact between a wearer's skin and urine/feces, and which can be produced at a low cost, can be obtained by an absorbent article including: an absorbent article body part that has a first leak preventer in sheet form and an absorber capable of absorbing a bodily fluid, wherein at least one layer thereof is arranged above the first leak preventer; a second leak preventer in sheet form that is arranged, above the absorber, from a middle part to a rear end part of the absorbent article body part, wherein a periphery part except for a front end part is sealed to the absorbent article body part so as to form an enclosed space in bag form on a lower side; a skin contact sheet that is arranged, above the second leak preventer, between a front part of the absorbent article body part and a rear part of the absorbent article body part, and that makes contact with a wearer's skin and that is spaced apart from the absorber at parts other than a front end part and a rear end part, at the time of use; and a urine/feces separation member in sheet form, wherein a front part or a middle part thereof couples to a part of the skin contact sheet corresponding to a crotch part, a rear part thereof extends, on a lower side of the second leak preventer, up to at least the front end part of the second leak preventer, and right and left side parts thereof couple to the absorbent article body part, and then completed the present invention.

Namely, the present invention provides the following (1) to (7):

(1) An absorbent article including:
an absorbent article body part that has a first leak preventer in sheet form and an absorber capable of absorbing a bodily fluid, wherein at least one layer thereof is arranged above the first leak preventer;
a second leak preventer in sheet form that is arranged, above the absorber, from a middle part to a rear end part of the absorbent article body part, the second leak preventer having an enclosed space formed in bag form on a lower side by sealing a periphery part except for a front end part to the absorbent article body part;
a skin contact sheet that is arranged, above the second leak preventer, between a front part of the absorbent article body part and a rear part of the absorbent article body part, and that makes contact with a wearer's skin and that is spaced apart from the absorber at parts other than a front end part and a rear end part, at the time of use; and
a urine/feces separation member in sheet form, wherein a front part or a middle part thereof couples to a part of the skin contact sheet corresponding to a crotch part, a rear part thereof extends, on a lower side of the second leak preventer, up to at least the front end part of the second leak preventer, and right and left side parts thereof couple to the absorbent article body part.

(2) The absorbent article according to section (1) above, wherein a part of a surface on an upper side of the rear part of the urine/feces separation member and a part of a surface on the lower side of the second leak preventer are coupled to each other.

(3) The absorbent article according to section (1) or (2) above, wherein the urine/feces separation member is coupled to leg gathers that is provided so as to extend in a front-rear direction of the absorbent article body part.

(4) The absorbent article according to one of sections (1)-(3) above, wherein a part forward of a part of the urine/feces separation member, which couples to the skin contact sheet, hangs down to a lower side of a urine permeation opening.

(5) The absorbent article according to one of sections (1)-(4) above, wherein the urine/feces separation member is a composite of a film and a hydrophilic non-woven fabric.

(6) The absorbent article according to one of sections (1)-(5) above, wherein a length in a front-rear direction of the urine/feces separation member is 50 to 200 mm and a width in a lateral direction thereof is 30 to 100 mm.

(7) The absorbent article according to one of sections (1)-(6) above, wherein the skin contact sheet is a sheet having a urine permeation opening in a front body part and a feces permeation opening in a rear body part.

Effect of the Invention

The absorbent article according to the present invention has no positional displacement at a crotch part of a skin contact sheet, is capable of effectively avoiding contact between a wearer's skin and urine/feces and can be produced at a low cost.

BRIEF DESCRIPTIONS OF THE DRAWINGS

FIG. 1 contains schematic diagrams illustrating an example of an absorbent article according to the present invention.

Figure 2:
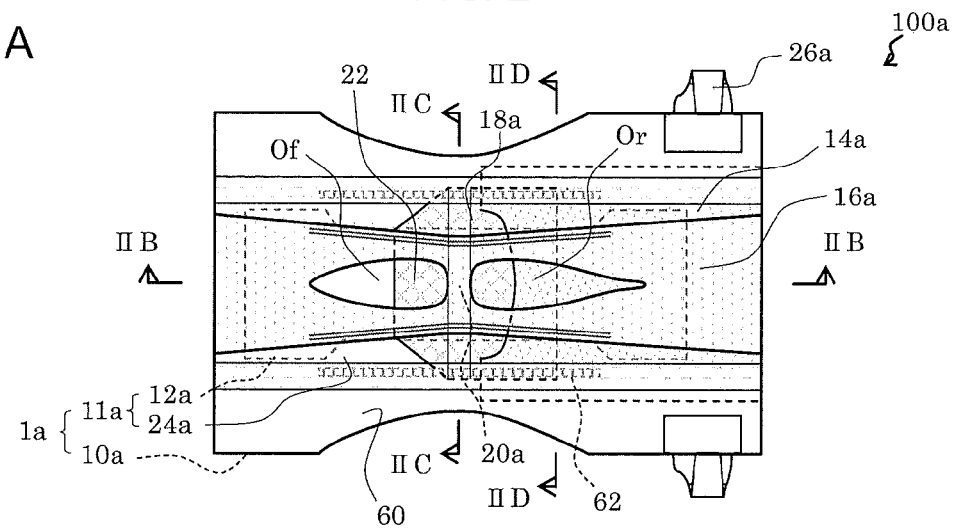
Figure 2:
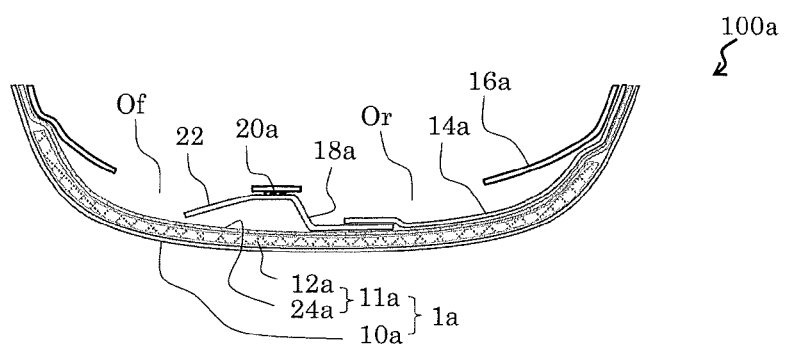
Figure 2:
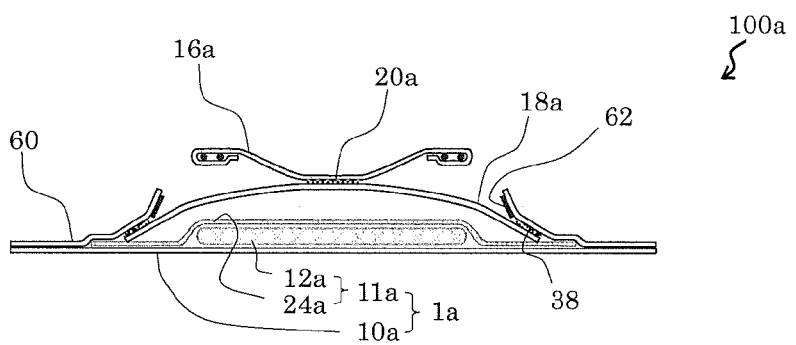
Figure 2:
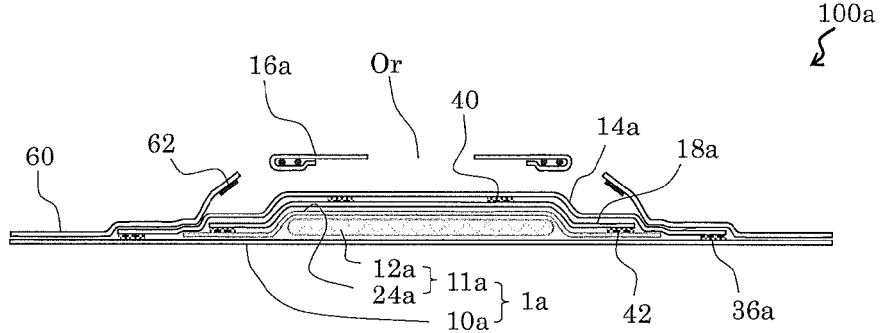

FIG. 2 contains schematic diagrams illustrating another example of an absorbent article according to the present invention.

Figure 3:
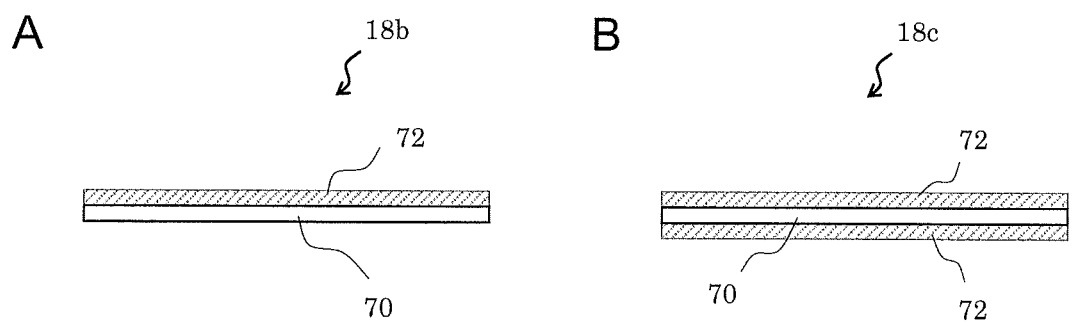

FIG. 3 contains schematic sectional views illustrating various examples of a urine/feces separation member.

Figure 4:
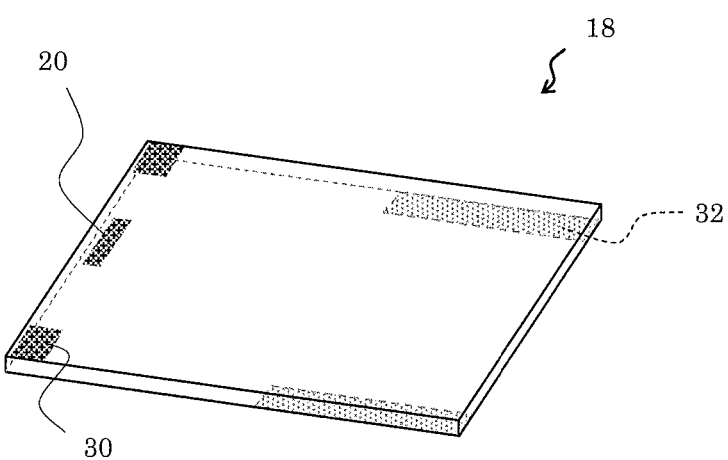
Figure 4:
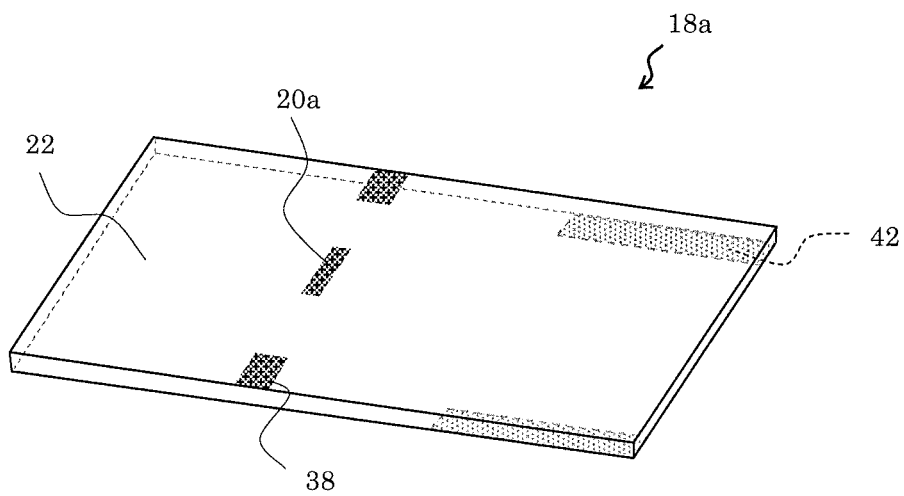

FIG. 4 contains schematic perspective views illustrating various examples of a urine/feces separation member.

Figure 5:
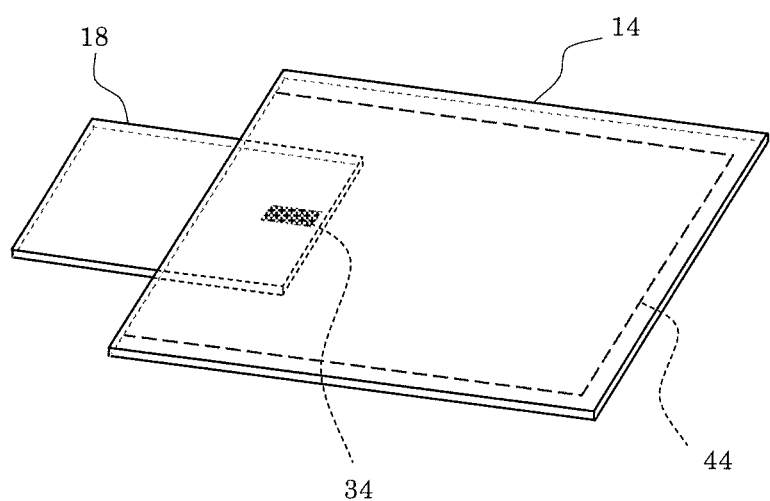
Figure 5:
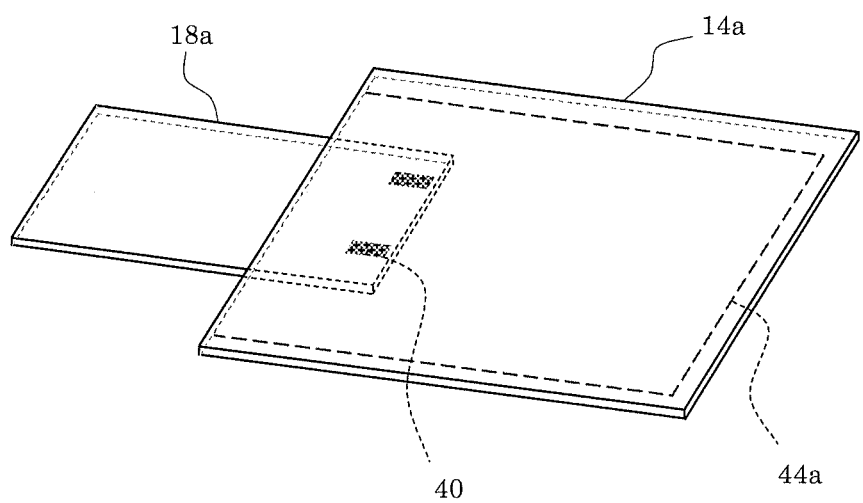

FIG. 5 contains schematic perspective views illustrating various examples of a combination of a urine/feces separation member and a second leak preventer.

EMBODIMENTS OF THE INVENTION

Hereinafter, the absorbent article according to the present invention will be described in detail, based on the preferred embodiments illustrated in the attached drawings. It should be noted that, in the present specification, when the absorbent article according to the present invention is actually worn, a side close to the skin of the wearer will be referred to as the "top/upper" and a side far therefrom will be referred to as the "bottom/under/lower." In addition, when the absorbent article according to the present invention is actually worn, a side corresponding to the front side of the wearer's body will be referred to as the "front" and a side corresponding to the back side thereof will be referred to as the "rear." Moreover, in order to facilitate understanding, in the respective drawings, members that are actually in contact with each other may be illustrated such that they are spaced apart. In the respective plan views among the attached drawings, the front side of the absorbent article, etc. is illustrated such that it is positioned on the left side of the corresponding drawing. In the respective longitudinal end face views and longitudinal sectional views among the attached drawings, the front side of the absorbent article, etc. is illustrated such that it is positioned on the left side of the corresponding drawing.

FIG. 1 contains schematic diagrams illustrating an example of an absorbent article according to the present invention. FIG. 1(A) is a plan view thereof, FIG. 1(B) is a longitudinal sectional view thereof along line IB-IB in FIG. 1(A), FIG. 1(C) is lateral sectional view thereof along line IC-IC in FIG. 1(A), and FIG. 1(D) is a lateral sectional view thereof along line ID-ID in FIG. 1(A).

Absorbent article 100 according to the present invention is configured as a tape-type diaper for infants having outer leg gathers (which are also referred to as "gusset gathers." Hereinafter referred to as "OLG"), which are present on both the right and left sides, and is basically provided with: absorbent article body part 1 having first leak preventer 10 in sheet form and absorber 11 which is capable of absorbing a bodily fluid, wherein at least one layer thereof is arranged above first leak preventer 10; second leak preventer 14 in sheet form, which is arranged, above absorber 11, from a middle part to a rear end part of absorbent article body part 1, wherein a periphery part, except for a front end part, is sealed to absorbent article body part 1 so as to form an enclosed space in bag form on the lower side; skin contact sheet 16, which is arranged, above second leak preventer 14, between a front part and a rear part of absorbent article body part 1 and which makes contact with a wearer's skin and is spaced apart from absorber 11 at parts other than a front end part and a rear end part, at the time of use; and urine/feces separation member 18 in sheet form, wherein a front part thereof couples to a part corresponding to a crotch part of skin contact sheet 16, a rear part thereof extends, on the lower side of second leak preventer 14, up to a front end part of second leak preventer 14, and the right and left side parts couple to absorbent article body part 1.

First, regarding absorbent article 100, the manner in which the members are arranged will be reviewed from the lower side toward the upper side.

Above first leak preventer 10 in sheet form, absorber 11, configured from absorber material 12 and top sheet 24, which covers the absorber material, is arranged so as to configure absorbent article body part 1. Above absorber 11, between the crotch part and the rear body, urine/feces separation member 18 having its front end part located at the crotch part and extending toward the rear body, and second leak preventer 14 having its front end part overlapping with a rear part of urine/feces separation member 18, are arranged so as to cover absorber 11. At the uppermost part, skin contact sheet 16 having urine permeation opening Of in the front body part and feces permeation opening Or in the rear body part is arranged from a front end part to a rear end part of absorbent article body part 1. Skin contact sheet 16 couples to absorbent article body part 1 at its front end part and rear end part. However, at parts other than the front end part and rear end part (i.e. parts between the front end part and rear end part), skin contact sheet 16 is separated from absorber 11 and is, on the whole, in a floating condition so that it is in constant contact with a wearer's skin. A crotch part of skin contact sheet 16 is coupled to the front end part of urine/feces separation member 18 and pulls up the front part of urine/feces separation member 18 to the upper side.

Next, the respective members, the relationship therebetween and their functions will be explained below.

As to the materials for each of first leak preventer 10 and second leak preventer 14, materials that are generally used as a back sheet may be used. In particular, a resin film made of, for example, PE, PP, PET, EVA or the like and a bodily fluid impermeable sheet, such as a foam sheet made of the resin described above, can be used. As for the bodily fluid impermeable sheet, a sheet having air permeability, such as an air permeable film or the like, may be preferably used.

In addition, when the above-described resin film is used, a multilayered sheet of such film and a non-woven fabric may be used in order to improve the texture and appearance. In this case, a spunbond (SB) or thermal bond non-woven fabric having a relatively low basis weight (for example, a spot-bond non-woven fabric made of PP) or the like may preferably be used as the non-woven fabric.

Moreover, a multilayered sheet of such resin film and an absorber in sheet form, which is described below, may also be used.

Further, a high water-resistance non-woven fabric may also be used. Examples of such high water-resistance non-woven fabric include an SMS non-woven fabric having a degree of a water resistance of 100 mmH$_2$O or more and an SB non-woven fabric or the like in which pores in a microfiber web are filled with microfibrillated cellulose (MFC) or wax so as to provide such fabric with water resistance. In this case, a high water-resistance non-woven fabric may be used alone or may also be used as a multilayered sheet of the film and such high water-resistance non-woven fabric.

It is preferable for first leak preventer 10 and second leak preventer 14 to be made of the same material, in terms of good adherence property through making use of an adhesive such as a heat sealant.

Each of first leak preventer 10 and second leak preventer 14 may be configured from a plurality of members.

First leak preventer 10 is in sheet form; however, it is not particularly limited in terms of its shape, as long as it accommodates absorber 11, etc. above thereof and allows skin contact sheet 16 to be arranged thereon.

Second leak preventer 14 is in a sheet form; however, it is not particularly limited in terms of its shape, as long as it is capable of receiving feces.

According to the present invention, a feces receiving sheet may be provided above the second leak preventer. In this case, such feces receiving sheet directly receives feces. Such feces receiving sheet may be detachably provided. In this case, when defecation occurs, the feces receiving sheet may be changed to an unused sheet and thus, the absorbent article according to the present invention can be used repeatedly until the urine absorption capacity reaches to full capacity.

The periphery part, except for the front end part, of second leak preventer 14 is sealed to absorbent body part 1 and an enclosed space in bag form is formed on the lower side of second leak preventer 14. Owing to this, even when, for example, the amount of the excreted urine reaches close to a limit of the absorption capacity of absorber 11 due to prolonged usage or the like, the urine, which is not absorbed and thus stays at the rear body part of absorber 11, does not seep out from a gap present at the periphery part of second leak preventer 14 toward a top part, i.e. onto second leak preventer 14, and thus, contact between urine and feces can be extremely effectively suppressed.

In particular, as shown in FIG. 1(B), in a front-rear direction, second leak preventer 14 covers absorber 11 and a rear end part of urine/feces separation member 18, and couples to first leak preventer 10, via top sheet 24, at a rear end part of absorbent article body part 1. In addition, as shown in FIG. 1(D), in a lateral direction, second leak preventer 14 couples to first leak preventer 10, via top sheet 24, at coupling part 36. In this way, second leak preventer 14 is sealed to absorbent article body part 1 on three sides, i.e. at the right and left edge parts and the rear end edge part thereof and thus, an enclosed space in bag form is formed on the lower side of second leak preventer 14.

The sealing method is not particularly limited and, for example, the coupling method may be achieved with an adhesive.

Absorber 11 used in the present invention is configured by covering absorber material 12 with top sheet 24.

According to the present invention, the absorber is not particularly limited, as long as it is capable of absorbing a bodily fluid, and any absorber used in publicly-known conventional absorbent articles may be used. In addition, an absorber material may be used as is or the absorber may be configured by covering the absorber material with a top sheet. For example, powdery wooden pulp, a powdery absorber (such as raw SAP, etc.) or an absorber in sheet form may be used as is, or it may be used after being coated with a top sheet.

An absorber in sheet form excels in morphological stability and capability of SAP fall prevention, etc.

Among various types of absorber in sheet form, a super absorbent sheet containing 50 mass % or more, preferably 60 mass % or more, or more preferably 70 mass % or more of SAP is preferred. In addition, from the perspective of stability, etc. of the super absorbent sheet, the content of SAP therein is preferably 95 mass % or less.

The super absorbent sheet is an extremely-thin absorber in sheet form having SAP as a primary component. Since the content of SAP is extremely high, the thickness of the super absorbent sheet is extremely low. The thickness of the super absorbent sheet is preferably 1.5 mm or less and more preferably 1 mm or less.

The super absorbent sheet is not particularly limited in terms of its configuration and production method, as long as it is an extremely-thin absorber in sheet form having SAP as a primary component.

For example, there is a super absorbent sheet obtained by an Air-Laid process. In the Air-Laid process, crushed wooden pulp and SAP are mixed and a binder is added to shape the mixture into a sheet form and then a super absorbent sheet is obtained. As examples of a super absorbent sheet obtained through this process, NOVATHIN (US trademark) manufactured by Rayonier Inc. in the US and B-SAP manufactured by Oji Kinocloth Co., Ltd., are known.

Another example of the super absorbent sheet includes a super absorbent sheet obtained through a process involving coating a bodily fluid permeable sheet such as a non-woven fabric with SAP-dispersed slurry. Here, the SAP-dispersed slurry is preferably prepared by dispersing SAP and microfibrillated cellulose (MFC) in a mixed solvent of water and ethanol. As an example of the super absorbent sheet obtained through this process, MegaThin (trademark) manufactured by Japan Absorber Technology Institute is known.

Other examples of the super absorbent sheet include: a super absorbent sheet obtained through a process involving having a raised non-woven fabric carry a large amount of SAP and fixing the SAP with a hot melt binder, an emulsion binder, an aqueous fiber, or the like; a super absorbent sheet obtained through a process involving mixing fibrous SAP with a PET (polyethylene terephthalate) fiber and forming the mixture into a web; and an SAP sheet, in which an SAP layer is sandwiched by tissues from the top and bottom.

Absorber 11 has top sheet 24 that covers absorber material 12. By way of having top sheet 24, even when absorber 11 makes contact with a wearer's skin, the irritation caused therefrom is alleviated and the attachment of absorber material 12, such as SAP, etc., dropping out of absorber 11 to the skin can be prevented.

The top sheet is not particularly limited and, for example, any publicly-known conventional top sheet may be used. In particular, a non-woven fabric made of synthetic fibers, such as a PP non-woven fabric, a PET non-woven fabric, a PE non-woven fabric, or the like, may be used. In addition, a non-woven fabric by Dry-Process which can be made by mixing a hydrophilic fiber, such as rayon, cotton and the like, and a synthetic fiber, may be used.

Top sheet 24 covers first leak preventer 10 from a middle part of a lateral direction of the first leak preventer up to the right and left edge parts.

Top sheet 24 is preferably coupled, at its surface, to a front end of skin contact sheet 16. For example, when skin contact sheet 16 is hydrophobic, skin contact sheet 16 can configure a front part pocket that performs a function of preventing seepage of urine from the front part.

At least one layer of absorber 11 is arranged above first leak preventer 10. Namely, absorber 11 may be comprised of one layer or two or more layers (multilayer).

In addition, absorber 11 may be arranged in a folded condition.

In absorbent article 100 according to the present invention, since absorber 11 is arranged from a front part of a top part of first leak preventer 10 to a lower side of second leak preventer 14, the urine absorption amount is significantly large, as compared to a method in which urine and feces are separated by a separation member and urine is absorbed only at a front part. In addition, since urine is absorbed by the entire surface of absorber 11, blockage is unlikely to occur even when a large amount of urine is excreted all at once.

In one of the preferred embodiments, part of the absorber is covered with a liquid guide sheet having a flow path which allows for transfer of urine therethrough.

The liquid guide sheet is not particularly limited, as long as it has a configuration in which a flow path which allows for transfer of urine therethrough is provided; however, it preferably has no bodily liquid absorption or bodily fluid retaining properties so that the transfer of urine can be carried out promptly. In particular, a concave-convex sheet member having holes at convex parts (i.e. a perforated concave-convex sheet member) may be given as a preferable example.

At least one surface of the perforated concave-convex sheet member is a concave-convex surface having concave parts and convex parts. In the perforated concave-convex sheet member, a multitude of concave parts, in connection with each other, function as a flow path for a bodily fluid. The perforated concave-convex sheet member has an advantage to the effect that the circulation of the bodily fluid is not disturbed even when the convex parts are crushed to a certain degree at the time of use.

In addition, in the perforated concave-convex sheet member, the holes also function as a flow path for a bodily fluid.

As for the materials for the perforated concave-convex sheet member, a bodily fluid impermeable film comprised of a resin made of, for example, PE, PP, PVA, urethane, or the like, may be given as an example.

As for a specific example of the perforated concave-convex sheet member, the member proposed in WO02/065965 by the present inventors may be given as an example.

When the perforated concave-convex sheet member is used as a guide sheet, a liquid residue where the bodily fluid remains in the holes occurs and a so-called re-wet value may become worse. In this case, on the lower side of the perforated concave-convex sheet member, a hydrophilic diffusion sheet may preferably be used in combination therewith. In this way, the bodily fluid present in the holes transfers by penetrating into such hydrophilic diffusion sheet and thus, the re-wet value will be significantly reduced. In addition, displacement between the perforated concave-convex sheet member and the leak preventer is prevented and thus, morphological stability is improved.

As shown in FIG. 1, skin contact sheet 16 is arranged, above absorber 11, between a front part of absorbent article body part 1 and a rear part of absorbent article body part 1. The configuration of skin contact sheet 16 is not particularly limited, as long as it makes contact with a wearer's skin and is spaced apart from absorber 11 at parts other than a front end part and a rear end part, at the time of use. For example, as shown in FIG. 1, a configuration in which the length of the two parts of skin contact sheet 16, which respectively couple to the front part and rear part of first leak preventer 10, is made smaller than the length of first leak preventer 10 corresponding to these parts, may be given as an example.

In addition, the skin contact sheet preferably has stretchability so as to facilitate constant contact with the wearer's skin. For providing stretchability, examples of implementation include configuring the skin contact sheet itself with a knit, a net, a non-woven fabric, or the like, made of a stretchable member such as a polyurethane filament, or the like having stretchability, and bonding a stretchable member to each side edge of the skin contact sheet. More particularly, for example, as the skin contact sheet described in Patent Document 1, a skin contact sheet having a configuration in which an elastic member is bonded and in which such elastic member is stretched in use and abuts the wearer's skin in a closely-attached condition may be used.

Since the skin contact sheet makes direct contact with the wearer's skin, the material configuring the skin contact sheet is preferably low irritative, and the surface thereof is smooth and soft and does not become sticky to the skin even when sweat is absorbed.

In particular, examples of the material configuring the skin contact sheet preferably include: a mesh made of filaments of, for example, PE, PP, PET, nylon, or the like; a non-woven fabric such as an air-through non-woven fabric, a spunmelt non-woven fabric and a spunlace non-woven fabric or the like, which makes use of fine synthetic fibers (preferably 5 denier or less) as raw materials; a perforated processed article of the above-described non-woven fabric; and a ribbed processed article of the above-described non-woven fabric.

Since the skin contact sheet makes direct contact with the wearer's skin, the surface of the materials above is preferably sweat-absorbent. In particular, examples thereof include: a sheet where a surface-hydrophilization treatment is applied to a non-woven fabric configured from synthetic fibers; and a sheet having a two-layered configuration of a hydrophilic non-woven fabric at the top and a hydrophobic non-woven fabric at the bottom.

Skin contact sheet 16 shown in FIG. 1 is a sheet having urine permeation opening Of in the front body part and feces permeation opening Or in the rear body part.

By providing skin contact sheet 16 with such configuration having urine permeation opening Of and feces permeation opening Or, it is possible to broadly cover absorber 11 by parts other than these openings. Thus, absorber 11 and skin contact sheet 16 are usually spaced apart. However, even when absorber 11 deforms and approaches the wearer depending on his/her body position or the like, skin contact sheet 16 serves to reduce the area of the wearer's skin which is in direct contact with absorber 11.

In one of the preferred embodiments, the skin contact sheet has one or both of the urine permeation opening and the feces permeation opening as described above.

The urine permeation opening corresponds to an opening for passing urine excreted from the urethral meatus when the absorbent article according to the present invention is used as an absorbent article for females and the urine permeation opening accommodates a penis or a penis and testicles when the absorbent article according to the present invention is used as an absorbent article for males.

The shape of the urine permeation opening is not particularly limited, as long as it performs the above-described function. For example, as shown in FIG. 1, a triangular notch with rounded angles formed in the front body of the skin contact sheet may be given as an example. The shape of the notch is not particularly limited and a circular or rectangular notch may be formed in addition to the above. Instead of a notch, it may be a slit provided in the skin contact sheet.

The feces permeation opening allows the feces excreted by the wearer to penetrate therethrough, and the feces are received on the second leak preventer.

The shape of the feces permeation opening is not particularly limited, as long as it performs the above-described function. For example, as shown in FIG. 1, a triangular notch with rounded angles formed in the rear body of the skin contact sheet may be given as an example. The shape of the notch is not particularly limited and a circular or rectangular notch may be formed in addition to the above.

Examples of embodiments of a skin contact sheet without a urine permeation opening and a feces permeation opening include an embodiment which is a sheet in which the front part and/or rear part of the skin contact sheet is/are deeply hollowed up to the position where urine or feces will be excreted and an embodiment in which the skin contact sheet has a plurality of bands (for example, a total of two bands on both sides) and the position where urine or feces will be excreted corresponds to the gap between the bands.

Among the various skin contact sheets described above, a sheet having both a urine permeation opening and feces permeation opening is preferable with respect to the point that contact between the absorber and the wearer's skin can be effectively prevented.

In absorbent article 100, skin contact sheet 16 couples to a rear end of second leak preventer 14. In this case, second leak preventer 14 can configure a rear part pocket which performs a function of preventing seepage, etc. of feces, in particular soft feces, from the rear part.

Urine/feces separation member 18 is in sheet form, and the front part thereof couples to a part of skin contact sheet 16 corresponding to the crotch part of the wearer at the time of use and the right and left side parts thereof couple to absorbent article body part 1.

Urine/feces separation member 18 is pulled up by the part of skin contact sheet 16 corresponding to the crotch part (namely, the part corresponding to the crotch part of the wearer when the wearer wears the absorbent article according to the present invention), and separates an internal space of the absorbent article into a front space and a back space. This can effectively prevent the mixing of urine and feces when such urine excreted onto absorber 11 in the front body transfers to second leak preventer 14 that accommodates feces in the rear body and the mixing of urine and feces when such feces (in particular, a liquid component thereof) excreted onto second leak preventer 14 in the rear body transfers to the front body part where urine is excreted.

In addition, since urine/feces separation member 18 couples to skin contact sheet 16 at the front part thereof and the right and left side parts thereof couple to absorbent article body part 1, the positional displacement of skin contact sheet 16 in the lateral and front-rear directions is suppressed. Namely, the positional displacement, which is a problem in the absorbent articles of Patent Documents 1 to 3, is solved in the absorbent article according to the present invention.

A top surface of the front end part of urine/feces separation member 18 is coupled to an under surface of the part of skin contact sheet 16 corresponding to the crotch part of the wearer at coupling part 20.

The coupling method is not particularly limited and, for example, the coupling method may be achieved with an adhesive.

Although urine/feces separation member 18 shown in FIG. 1 couples to the under surface of skin contact sheet 16 at coupling part 20, the present invention is not limited thereto. For example, the urine/feces separation member may be coupled to a top surface of the part of the skin contact sheet corresponding to the crotch part of the wearer.

In addition, in urine/feces separation member 18 shown in FIG. 1, the top surface thereof couples to the under surface of skin contact sheet 16; however, the present invention is not limited thereto. For example, the front end part of the urine/feces separation member is folded up and the coupling with the part of the skin contact sheet corresponding to the crotch part of the wearer may be made at such folded-up part.

The position of coupling between the urine/feces separation member and the skin contact sheet is not particularly limited. For example, as in the case of absorbent article 100, such position may be at the middle part in the lateral direction of the front part of urine/feces separation member 18 and also at the middle part in the lateral direction of skin contact sheet 16. In this case, since the stretchability in the lateral direction of skin contact sheet 16 is not disturbed, a condition can be achieved in which skin contact sheet 16 is closely attached to the wearer's skin and is spaced apart from absorber 11, while it does not displace in the lateral direction.

In addition, the right and left side parts of urine/feces separation member 18 are coupled to absorbent article body part 1.

The coupling method is not particularly limited and, for example, the coupling method may be achieved with an adhesive.

In particular, the right and left side parts of the front end part of urine/feces separation member 18 are coupled to parts folded back at the right and left side parts of absorbent article body part 1, at coupling parts 30, in the vicinity of the roots of the OLGs formed by first leak preventer 10 and top sheet 24 sandwiching a plurality of pieces of yarn-like rubber 50 therebetween (see FIG. 1(C)). In addition, the right and left side parts of the rear end part of urine/feces separation member 18 are coupled to absorbent article body part 1 at coupling parts 32 (see FIG. 1(D)). Coupling part 30 and coupling part 32 may be independent from each other or may integrally form a coupling part.

In absorbent article 100, urine/feces separation member 18 is coupled to the OLGs in the vicinity thereof. An embodiment in which the urine/feces separation member is coupled to the leg gathers, which are provided so as to extend in the front-rear direction of the absorbent article body part, as described above, is one of the preferred embodiments. In this embodiment, since the transfer of urine or the like on the right and left sides of urine/feces separation member 18 can be effectively suppressed, the urine and feces separation function is superior. In addition, in this embodiment, the effect of stabilizing the steric structure of the folded OLG is also obtained.

The leg gather is not particularly limited and, for example, a leg gather similar to the leg gather in the publicly-known conventional absorbent article may be used.

Leg gathers are generally classified into two types. One type is an OLG which is present on both the right and left side edges of the absorbent article body. The other is an inner leg gather (also referred to as a "standing leg gather." Hereinafter referred to as an "ILG") which is provided inside the absorbent article and sterically rises from both sides of the absorber configured from a super absorbent polymer, pulp or the like.

The absorbent article according to the present invention may have one or both of the OLG and ILG. When the absorbent article according to the present invention only has an OLG, one of the preferred embodiments thereof is an embodiment in which of the urine/feces separation member is coupled to part of the OLG, as with absorbent article 100. When the absorbent article according to the present invention only has an ILG, one of the preferred embodiments thereof is an embodiment in which the urine/feces separation member is coupled to part of the ILG, as with absorbent article 100a described below. When the absorbent article according to the present invention has both an OLG and ILG, one of the preferred embodiments thereof is an embodiment in which the urine/feces separation member is coupled to the ILG.

Furthermore, the rear part of urine/feces separation member 18 extends, on the lower side of second leak preventer 14, up to the front end part of second leak preventer 14 and part of the top surface of the extended part and part of the under surface of second leak preventer 14 are coupled to each other at coupling part 34 (see FIGS. 1(B) and 1(D)). When urine/feces separation member 18 and second leak preventer 14 are coupled to each other in this way, the position of urine/feces separation member 18 is stabilize and thus, the positional displacement of skin contact sheet 16 coupled to the urine/feces separation member can be more effectively suppressed.

The position of the coupling part between the urine/feces separation member and the second leak preventer is not particularly limited. For example, as in the case of absorbent article 100, such position may be at the middle part in the lateral direction of the rear part of urine/feces separation member 18.

As described above, since urine/feces separation member 18 is coupled to skin contact sheet 16 at the front part thereof, it is picked upward (i.e. a lift-up effect) by skin contact sheet 16 floating upward at the time of use and it stands up at the crotch part as shown in FIG. 1(B).

Accordingly, urine/feces separation member 18 does not require self-standing properties and thus, use of a stretchable material is not necessary, and a sheet or the like, such as a simple non-woven fabric or the like, may be used for the material. Accordingly, the material costs can be reduced and production apparatuses can be simplified, and thus, the production costs can also be reduced.

The material configuring the urine/feces separation member is preferably liquid impermeable, with respect to the point that the above-described urine and feces separation effect can be improved even more.

On the other hand, the material configuring the urine/feces separation member is preferably hydrophilic at a surface thereof where contact is made with the absorber. When the surface is hydrophilic, the effect of the absorber guiding urine rearward, which will be described below, becomes significant.

In particular, in one of the preferred embodiments, such material is a composite of a film and a hydrophilic non-woven fabric. In one of more preferred embodiments, such material is a composite in which hydrophilic non-woven fabrics are bonded to the top surface and under surface of a film.

In addition, a stretchable material may be used for the material configuring the urine/feces separation member.

However, it is preferable not to make use of such stretchable material, with respect to the point that production can be performed at a low cost.

In the absorbent article described in Patent Document 4, it is substantially necessary to configure the bridging member by making use of a stretchable material for reasons such as to make the bridging member follow the movements of the wearer's body so as to maintain a condition in which such bridging member is in contact with the perineum of the wearer. However, in the absorbent article according to the present invention, since the skin contact sheet provides a function of maintaining a condition in which such skin contact sheet is in contact with the wearer's skin at the time of use, the urine/feces separation member can be configured solely with a non-stretchable material.

The configuration and shape of the urine/feces separation member will be described in detail later.

The rear end of urine/feces separation member 18 shown in FIG. 1 is placed above absorber 11.

When urine is excreted onto absorber 11 through urine permeation opening Of, part of such urine is absorbed by the part in the front body of absorber 11 and the greater part of such urine is absorbed by absorber 11 and, at the same time, transfers and moves through the gap between the top surface of absorber 11 and the under surface of second leak preventer 14. During this transfer, the rear end (corresponding to the part placed above absorber 11) of urine/feces separation member 18 provides a urine guiding function and promotes the rearward transfer of the urine, and thus, the usage efficiency of absorber 11 is increased.

As shown in FIG. 1, urine/feces separation member 18 extends up to the lower side of the front end part of second leak preventer 14.

In this way, in the absorbent article according to the present invention, the rear part of the urine/feces separation member extends, on the lower side of second leak preventer 14, up to at least the front end part of second leak preventer 14, and thus, a gap is ensured between the top surface of absorber 11 and the under surface of second leak preventer 14 and the rearward transfer of urine becomes smoother. In particular, it is preferable for a surface of urine/feces separation member 18 on the side of absorber 11 to be hydrophilic, since this effect will then be more significant.

In addition, even when the feces excreted onto second leak preventer 14 are watery, since the liquid component thereof can be guided rearward of absorber 11 and thus, mainly the solid content of the feces remains on second leak preventer 14, the leakage of soft feces can be prevented.

As shown in FIG. 1, the rear end part of urine/feces separation member 18 is preferably spaced apart from the front end part of second leak preventer 14.

In this way, even when the feces excreted onto second leak preventer 14 are watery, since the liquid component thereof can be guided to absorber 11 and thus, mainly the solid content of the feces remains on second leak preventer 14, the leakage of soft feces can be prevented, and at the same time, a feeling of discomfort due to the contact between the wearer's skin and the liquid component can be alleviated.

It is preferable for the urine/feces separation member to be coupled to the absorber, provided that the above-described effect of moving urine rearwards is not compromised. In this way, the position of the urine/feces separation member at the time of use becomes more stable.

The coupling method is not particularly limited and, for example, the coupling method may be achieved with an adhesive.

It should be noted that, in the present invention, regarding the coupling between the absorber and the urine/feces separation member, when the absorber material is exposed, such coupling refers to the coupling between the surface on the upper side of the absorber material and the urine/feces separation member, and when a top sheet (for example, top sheet 24 shown in FIG. 1) or an acquisition layer, which is bonded to the surface of the absorber material, is present, such coupling refers to the coupling between the surface on the upper side of such top sheet or acquisition layer and the urine/feces separation member.

When the urine/feces separation member is applied to a paper diaper for infants, the length in the front-rear direction is preferably 50-200 mm and the width in the lateral direction is preferably 30-100 mm. Within such ranges, the urine/feces separation member can be easily incorporated into the production process and the material will not be wasted.

The width in the lateral direction of part of a urine/feces separation member, which is placed above the absorber, is, as with urine/feces separation member 18, preferably larger than the width in the lateral direction of the absorber of the corresponding part so that the top surface of the absorber is not exposed. In this way, the transfer of urine in the lateral direction is suppressed and the leakage can be prevented.

Detachable members 26 are provided on both the right and left sides in the vicinity of the rear end of first leak preventer 10. On the under surface in the vicinity of the front end of first leak preventer 10, detachable members (not shown) are provided such that they can be detached from detachable members 26. These detachable members may be configured by, for example, various hook-and-loop fasteners.

The size of absorbent article 100 shown in FIG. 1 is not particularly limited.

FIG. 2 contains schematic diagrams illustrating another example of an absorbent article according to the present invention. FIG. 2(A) is a plan view thereof, FIG. 2(B) is a longitudinal sectional view thereof along line IIB-IIB in FIG. 2(A), FIG. 2(C) is a lateral sectional view thereof along line IIC-IIC in FIG. 2(A) and FIG. 2(D) is a lateral sectional view thereof along line IID-IID in FIG. 2(A).

Absorbent article 100a shown in FIG. 2 is basically similar to absorbent article 100, except for the shape of urine/feces separation member 18a being different from that of urine/feces separation member 18 and for absorbent article body part 1a having side sheet 60 and urethane film 62 that form an ILG, instead of yarn-like rubber 50 that forms the OLG.

It should be noted that absorbent article body part 1a, first leak preventer 10a, absorber 11a, absorber material 12a, second leak preventer 14a, skin contact sheet 16a, coupling part 20a, top sheet 24a, detachable member 26a and coupling part 36a in absorbent article 10a differ with respect to details such as shape, etc.; however, they respectively correspond to absorbent article body part 1, first leak preventer 10, absorber 11, absorber material 12, second leak preventer 14, skin contact sheet 16, coupling part 20, top sheet 24, detachable member 26 and coupling part 36 in absorbent article 100 (it should be noted that coupling part 36a directly couples first leak preventer 10a and second leak preventer 14a with each other).

The shape and function of the front part of urine/feces separation member 18a are different from those of urine/feces separation member 18.

More specifically, the middle part of urine/feces separation member 18a couples to the part of skin contact sheet 16a, which corresponds to the crotch part of the wearer, at coupling part 20a, and hanging part 22, which is forward of coupling part 20a coupling with skin contact sheet 16a, hangs down to the lower side of urine permeation opening Of. This hanging part 22 forms a flow path when the urine excreted from the wearer transfers to absorber 11.

In this way, when the part that is forward of the part of the urine/feces separation member that couples to the skin contact sheet hangs down to the lower side of the urine permeation opening, a smooth transfer of urine to the absorber 12 is obtained.

In particular, when the absorbent article according to the present invention is intended for females, by allowing the part of skin contact sheet 16a corresponding to the crotch part of the wearer to make contact with the perineal region and by allowing hanging part 22 of urine/feces separation member 18a to make contact with the female genitals, the contact area is increased and thus, urine can be collected in a stable manner. Further, the position of the absorbent article at the time of use becomes more stable and the contact with absorber 11a is more effectively prevented, and thus, such absorbent article is useful.

Urine/feces separation member 18a couples to the inner side of an ILG, which will be described below, at coupling part 38. In this way, the transfer of urine or the like on both the right and left sides of urine/feces separation member 18a can be effectively suppressed, and thus, the urine and feces separation function becomes superior.

The shape and function of the rear part of urine/feces separation member 18a are substantially similar to those of urine/feces separation member 18; however, the positions and the numbers of the same which couple to second leak preventer 14a are different.

More specifically, the rear part of urine/feces separation member 18a couples to second leak preventer 14a at a total of two coupling parts 40, one each on both the right and left sides of such rear part.

The rear part of urine/feces separation member 18a couples to the parts present on the right and left edge parts of top sheet 24a of absorber 11a at a total of two coupling parts 42, one each on both the right and left sides of such rear part.

Additionally, in absorbent article 100a, the middle part in the lateral direction of first leak preventer 10a is covered with top sheet 24a; however, top sheet 24a does not cover up to the right and left edge parts of first leak preventer 10a and the right and left edge parts of first leak preventer 10a are covered with side sheet 60.

Side sheet 60 stands up as it goes inward and has urethane film 62, on its inner surface, extending in the front-rear direction. An ILG is configured by this side sheet 60 and urethane film 62.

The position of where the ILG is arranged in absorbent article 100a differs from that in the publicly-known conventional absorbent article. Namely, the ILG of absorbent article 100a is arranged so that it is located outward of skin contact sheet 16a so that it does not overlap with skin contact sheet 16a. The ILG of the publicly-known conventional absorbent article is often arranged inward of the left and right edge parts of the absorber. However, the ILG of absorbent article 100a is arranged outward of the part where absorber material 12a of absorber 11a is present.

Hereinafter, the urine/feces separation member and the second leak preventer used in the absorbent article according to the present invention will be described in detail.

The urine/feces separation member used in the absorbent article according to the present invention is, as described above, preferably liquid impermeable. For example, a liquid impermeable film, a non-woven fabric or the like may be used.

In particular, a liquid impermeable material with a hydrophilic surface is preferable with respect to the point that it allows a smooth diffusion of bodily liquid to occur over the surface of urine/feces separation member. Specifically, a configuration in which a hydrophilic material is arranged on the surface of the liquid impermeable material is preferable.

FIG. 3 contains schematic sectional views illustrating various examples of a urine/feces separation member.

Urine/feces separation member 18b shown in FIG. 3(A) has a two-layer configuration in which hydrophilic material 72 in sheet form is layered onto liquid impermeable material 70 in sheet form.

Urine/feces separation member 18c shown in FIG. 3(C) has a three-layer configuration in which hydrophilic materials 72 in sheet form are layered onto and under liquid impermeable material 70 in sheet form.

Examples of liquid impermeable materials include: a liquid impermeable film made of, for example, PE, PP, PET or the like; a water-resistant spunmelt non-woven fabric such as a PP-based SMS non-woven fabric, a PE/PP-based SB non-woven fabric, or the like; and a water-repellent resin-processed article of a non-woven fabric.

Examples of hydrophilic materials include: tissue paper; a spunlace non-woven fabric mixed with rayon, cotton, or the like; a hydrophilic non-woven fabric such as TCF®, Bemliese®, or the like; and a non-woven fabric having its surface hydrophilization-processed through surfactant treatment of a hydrophobic synthetic non-woven fabric.

As for the urine/feces separation member, the liquid impermeable material and the hydrophilic material described above may be appropriately combined and used.

In addition, for example, a liquid impermeable material with a hydrophilic coating surface, which is obtained by coating MFC (microfibrillated cellulose) on only one surface of a PP-based SMS non-woven fabric, may be used for urine/feces separation member 18b shown in FIG. 3(A).

FIG. 4 contains schematic perspective views illustrating various examples of a urine/feces separation member.

Urine/feces separation member 18 shown in FIG. 4(A) corresponds to the urine/feces separation member used in absorbent article 100 shown in FIG. 1

Urine/feces separation member 18 has a substantially rectangular shape.

Urine/feces separation member 18 has coupling part 20 that is coupled to skin contact sheet 16, at the middle part in the lateral direction of the top surface of the front end part of such member (see FIGS. 1(B) and 1(C)). By being coupled to skin contact sheet 16 at this coupling part 20, urine/feces separation member 18 has a configuration where it stands up toward the upper side.

In addition, urine/feces separation member 18 has coupling parts 30 that are coupled to folded-back parts of the OLGs formed by first leak preventer 10 and top sheet 24 sandwiching a plurality of pieces of yarn-like rubber 50 therebetween, at both the right and left edge parts of the top surface of the front end part of such member (see FIGS. 1(C) and 1(D)).

Moreover, urine/feces separation member 18 has coupling parts 32 that are coupled to absorbent article body part 1 (top sheet 24), at both the right and left edge parts of the under surface of the rear part of such member (see FIG. 1(D)).

Urine/feces separation member 18a shown in FIG. 4(B) corresponds to the urine/feces separation member used in absorbent article 100a shown in FIG. 2.

Urine/feces separation member 18a has a substantially rectangular shape but is relatively longer in the front-rear direction as compared to urine/feces separation member 18 and the front part thereof forms hanging part 22. As described above, this hanging part 22 is located directly under urine permeation opening Of of skin contact sheet 16a and provides a guiding function so that the excreted urine can be smoothly transferred over absorber 11a (FIGS. 2(A) and 2(B)).

Urine/feces separation member 18a has coupling part 20 that is coupled to skin contact sheet 16a, at the middle part in the lateral direction of the top surface of the middle part in the front-rear direction of such member (see FIGS. 2(B) and 2(C)). By being coupled to skin contact sheet 16a at this coupling part 20a, urine/feces separation member 18a has a configuration in which it stands up toward the upper side.

In addition, urine/feces separation member 18a has coupling parts 38 that are coupled to the ILGs configured by side sheet 60 and urethane film 62, at both the right and left edge parts of the top surface of the middle part in the front-rear direction of such member (see FIG. 2(C)).

Moreover, urine/feces separation member 18a has coupling parts 42 that are coupled to absorbent article body part 1a (top sheet 24a), at both the right and left edge parts of the under surface of the rear part of such member (see FIG. 2(D)).

The second leak preventer is in sheet form and is arranged, above the absorber, from the middle part of the absorbent article body part to the rear end part, and the periphery part except for the front end part is sealed to the absorbent article body part and an enclosed space in bag form is formed on the lower side.

FIG. 5 contains schematic perspective views illustrating various examples of a combination of a urine/feces separation member and a second leak preventer.

Urine/feces separation member 18 and second leak preventer 14 shown in FIG. 5(A) respectively correspond to the urine/feces separation member and second leak preventer used in absorbent article 100 shown in FIG. 1.

Second leak preventer 14 has a substantially rectangular shape.

Urine/feces separation member 18 and second leak preventer 14 are coupled at coupling part 34 in spot form.

The position of coupling part 34 is at the middle part in the lateral direction of the top surface of the rear end part of urine/feces separation member 18 and also the middle part in the lateral direction of the under surface of the front part of second leak preventer 14.

Second leak preventer 14 is sealed to absorbent article body part 1 at sealing part 44 (including coupling part 36) on three sides, i.e. at the rear end part and the right and left edge parts of such leak preventer. Specifically, second leak preventer 14 is coupled to top sheet 24 at the rear end part and the left and right end parts and is indirectly coupled to first leak preventer 10 via top sheet 24.

Urine/feces separation member 18a and second leak preventer 14a shown in FIG. 5(B) respectively correspond to the urine/feces separation member and second leak preventer used in absorbent article 100a shown in FIG. 2.

Second leak preventer 14a has a substantially rectangular shape.

Urine/feces separation member 18a and second leak preventer 14a are coupled at two coupling parts 40 in spot form.

The positions of the two coupling parts 40 are in the vicinity of the right and left edge parts of the top surface of the rear end part of urine/feces separation member 18a and also in the vicinity of the middle part in the lateral direction of the under surface of the front part of second leak preventer 14a. Due to the coupling in spot form at the two right and left locations, the rear end part of urine/feces separation member 18a is fixed, a space for allowing soft feces to transfer to the absorber present in the rear body is formed and a flow path is secured for urine that runs over urine/feces separation member 18a to the absorber present in the rear body.

Second leak preventer 14a is sealed to absorbent article body part 1a at sealing part 44a (including coupling part 36a) on three sides, i.e. at the rear end part and the right and left end parts of such leak preventer. Specifically, second leak preventer 14a is directly coupled to first leak preventer 10a at the right and left edge parts and is coupled to top sheet 24a at the rear end part, and is indirectly coupled to first leak preventer 10a via top sheet 24a.

The absorbent article according to the present invention is not particularly limited, as long as it is provided with: an absorbent article body part having a first leak preventer and an absorber; a second leak preventer; a skin contact sheet; and a urine/feces separation member, each of which are described above. For example, it may be further provided with various components of publicly-known conventional absorbent articles.

The absorbent article according to the present invention may be tape-type or in the form of underpants (i.e. tapeless).

As described above, the absorbent article according to the present invention is illustrated based on the respective embodiments illustrated herein; however, it should be noted that the present invention is not limited to these embodiments and, for example, the configurations of the respective parts may be replaced with any configuration capable of performing a similar function.

In addition, the configurations of the respective parts in the respective embodiments may be combined in an arbitrary manner to obtain other embodiments.

The absorbent article according to the present invention may be preferably used for paper diapers (for infants and adults), incontinence articles, training pants, or the like.

DESCRIPTIONS OF REFERENCE NUMERALS 1, 1a Absorbent article body part
10, 10a First leak preventer
11, 11a Absorber
12, 12a Absorber material
14, 14a, Second leak preventer
16, 16a Skin contact sheet
18, 18a, 18b Urine/feces separation member
20, 20a, 30, 32, 34, 36, 36a, 38, 40, 42 Coupling part
22 Hanging part
24, 24a Top sheet
26, 26a Detachable member
44, 44a Sealing part
50 Yarn-like rubber
60 Side sheet
62 Urethane film
70 Liquid impermeable material
72 Hydrophilic material
100, 100a, Absorbent article
Of Urine permeation opening
Or Feces permeation opening

The invention claimed is:
1. An absorbent article, comprising:
an absorbent article body having a first leak preventer sheet and an absorber configured to absorb bodily fluid, wherein at least one layer of the absorber is arranged above the first leak preventer;
a second leak preventer sheet that is arranged, above the absorber, from a middle part of the absorbent article body to a rear end part of the absorbent article body, the second leak preventer having a periphery sealed to the absorbent article body except for a front end part of the second leak preventer such that the second leak preventer cooperates with the absorbent article body to define an enclosed space below the second leak preventer with an opening at the front end part of the second leak preventer;

a skin contact sheet that is arranged, above the second leak preventer, between a front end part of the absorbent article body and the rear end part of the absorbent article body, and that, at the time of use, makes contact with a wearer's skin and is spaced apart from the absorber at parts of the absorbent article body other than the front end part of the absorbent article body and the rear end part of the absorbent article body; and a urine/feces separation member sheet, wherein (i) a front part or a middle part of the urine/feces separation member sheet is coupled to a crotch part of the skin contact sheet, (ii) a rear part of the urine/feces separation member sheet extends, on a lower side of the second leak preventer, up to at least the front end part of the second leak preventer, and (iii) right and left side parts of the urine/feces separation member sheet are coupled to the absorbent article body.

2. The absorbent article according to claim 1, wherein a part of a surface on an upper side of the rear part of the urine/feces separation member sheet and a part of a surface on the lower side of the second leak preventer are coupled to each other.

3. The absorbent article according to claim 1, wherein the urine/feces separation member sheet extends in a front-rear direction of the absorbent article body, and is coupled to leg gathers that are provided.

4. The absorbent article according to claim 1, wherein the middle part of the urine/feces separation member sheet is coupled to the crotch part of the skin contact sheet, and a part of the urine/feces separation member sheet that is forward of the middle part of the urine/feces separation member sheet hangs down to a lower side of a urine permeation opening in the skin contact sheet.

5. The absorbent article according to claim 1, wherein the urine/feces separation member sheet is a composite of a film and a hydrophilic non-woven fabric.

6. The absorbent article according to claim 1, wherein a length in a front-rear direction of the urine/feces separation member sheet is 50 to 200 mm, and a width in a lateral direction of the urine/feces separation member sheet is 30 to 100 mm.

7. The absorbent article according to claim 1, wherein a front part of the skin contact sheet has a urine permeation opening, and a rear part of the skin contact sheet has a feces permeation opening.

* * * * *